United States Patent
Joy

[11] 3,962,908
[45] June 15, 1976

[54] TRANSDUCER ARRANGEMENT FOR ULTRASONIC RAIL TESTER COUPLING CARRIAGES

[76] Inventor: Ivan L. Joy, 415 Delaware Drive, Ozawkie, Kans. 66070

[22] Filed: June 30, 1975

[21] Appl. No.: 591,819

Related U.S. Application Data

[63] Continuation-in-part of Ser. No. 445,080, Feb. 25, 1974, Pat. No. 3,937,068.

[52] U.S. Cl. .............................. 73/67.7; 73/71.5 US
[51] Int. Cl.² ........................................ G01N 29/04
[58] Field of Search ................. 73/67, 67.8 S, 67.7, 73/67.5 R, 67.9, 67.8 R, 71.5 US

[56] References Cited
UNITED STATES PATENTS

| | | | |
|---|---|---|---|
| 3,156,111 | 11/1964 | Joy | 73/67.8 S |
| 3,251,220 | 5/1966 | Joy | 73/71.5 US |
| 3,279,242 | 10/1966 | Megoloff | 73/71.5 US |

*Primary Examiner*—Richard C. Queisser
*Assistant Examiner*—Stephen A. Kreitman
*Attorney, Agent, or Firm*—Mann, Brown & McWilliams

[57] ABSTRACT

A transducer arrangement for ultrasonic rail tester coupling carriages comprising a first pair of flat angle signal transducers that are both connected to be senders and receivers and are directed in opposite directions lengthwise forwardly and rearwardly of the rail along the center of the rail head, a second pair of flat angle signal transducers that are both connected to be senders and receivers and are directly forwardly and rearwardly of the rail but are canted toward the rail gauge edge at preferred angle of 19°, and a third pair of flat angle signal transducers, one of which is a sender and the other of which is a receiver, that are canted toward the rail gauge edge at an angle of 80 or more degrees to provide a zig-zag signal path of multiple bounces across the rail head. The transducers act through transmitting wedges made of a material to be inefficient as a medium through which ultrasonic sound may be sent such that a significantly improved signal to noise ratio results.

18 Claims, 8 Drawing Figures

TRANSDUCER ARRANGEMENT FOR ULTRASONIC RAIL TESTER COUPLING CARRIAGES

This application is a continuation-in-part of my application Ser. No. 445,080 filed Feb. 25, 1974 now U.S. Pat. No. 3,937,068.

This invention relates to a transducer arrangement for ultrasonic rail flaw tester coupling carriages, and more particularly is directed to rail flaw tester equipment of the general type shown in my U.S. Pat. No. 3,251,220, granted May 17, 1966, the disclosure of which is hereby incorporated in its entirety by this reference.

My said U.S. Pat. No. 3,251,220 discloses apparatus for progressive flaw testing of railroad track rails utilizing ultrasonics, wherein separate coupler carriages are provided for coupling to each rail, which carriages are located in trailing relation to the rail car that is equipped with the ultrasonic machines and related equipment employed. The coupling carriages each provide a coupling trough for a series or array of ultrasonic signal sending and receiving transducers that are oriented at an angle of incidence in the range of 25° – 30° to inducing within the rail a shear wave travelling at a so-called "flat angle" in the range of 75° – 89°, relative to the plane of the rail head top surface, whereby the shear waves involved are oriented to be substantially normal of the flaws to be detected. Surface waves on the rail head top surface that tend to be generated by the use of such flat angles are damped by transmitting the ultrasonic signals involved through a diaphragm or a body of water on top of the rail, or through a diaphragm riding on a previously wetted rail head top surface. The ultrasonic machines involved are triggered in a predetermined cyclical sequence and the basic equipment involved is arranged to provide an integrated pictorial display of the intelligence received by the operation of the transducers.

These improvements permit practical rail flaw testing at flat angles of 80° to 85°; the nearly perpendicular path that the shear wave beams make toward the defect in the rail to be located provide a significant increase in the amount of energy reflected from the defect, and the signal has a fanning effect of approximately 15° for efficient scanning purposes.

In utilizing equipment of this type, it has been the practice to employ two transducers located at the center of the rail head and two transducers located half way between the gauge edge of the rail and the center of the rail, with the signals of the respective sending transducers being directed straight down the length of the track rail. While the flat angle pulse application of said patent sufficiently enhances ultrasonic testing efficiency to make it comparable to AAR on-rail type magnetic detector cars, difficulty has been experienced in locating small gauge edge defects lying in the lower corner of the rail head. This has been true in shelled and head checked areas and on worn curved rails.

Furthermore, ultrasonic testing has long been plagued by reflections due to conditions other than the presence of defects; these reflections, which are known as noise, are generated due to motion, grain size of the metal forming the rail, the wetting agent employed, and various relationships of moving variables in contact between the rail and the respective transducers. This problem has only been increased by attempts to build increased sensitivity into the components involved.

Another difficulty encountered utilizing electronics for rail flaw detection has been in locating a vertical split head that is located on one side of the rail head. Vertically acting transducers located at the center of the rail head can be relied on to find most vertical split heads that lie along the mid portion of the rail head. However, vertical splits in the head located at either side of the head may be missed, and while they are rather rare in occurrence, it is essential that they be located.

A principal object of the invention is to provide an improved transducer array arrangement for ultrasonic rail flaw tester carriages, which insures location of all small gauge edge defects lying in the lower corner of the rail head and vertical split heads which are present only on one side of the head or the other side of same, as well as the other types and kinds of defects that need to be located.

Another principal object of the invention is to operate the transducers through wedges formed from a material that is relatively inefficient as a medium through which to send sound to operate the transducer with a somewhat more narrow band width with the limiting of the band width also providing a more favorable signal to noise ratio.

Yet another principal object of the invention is to dispose the wedges at the angle of incidence, for transmital of the ultra sonic signal therethrough, for application to the rail, that for the particular material used to form the wedge, will provide the aforementioned desired flat angle signal paths within the rail.

Other objects of the invention are to generally improve ultrasonic coupler carriages of the type disclosed in my said patent, and to provide an ultrasonic coupling carriage arrangement that is economical of manufacture, efficient in use, and long lived in operation.

In accordance with this invention, a crystal array is provided in which the transducers employed are all arranged to provide the flat angle signal within the rail contemplated by my said patent, with the crystal array involved providing a first pair of transducers that are both connected to be senders and receivers and direct their beams in opposite directions lengthwise of the rail along the center line of the rail head forwardly and rearwardly of the rail head, a second pair of flat angle transducers that are both connected to be senders and receivers and are directed forwardly and rearwardly of the rail, but are oppositely canted toward the rail gauge edge at an angle that is preferably about 19 degrees, and a third pair of flat angle signal transducers, one of which is a sender and the other of which is a receiver, that are positioned in signal emitting and receiving relation to provide a zig-zag signal path of several bounces across the rail head leading from the emitting transducer to the receiving transducer. All the transducers involved in the array each act along the center of the rail head and through a transmitting wedge that is made of a material that is relatively inefficient as the medium for transmittal of ultrasonic sound to operate the respective transducers with a somewhat narrower band width than customary to provide a better signal to noise ratio.

All transducer wedges are oriented, with reference to the material that they form and the function that they serve, to provide operation at the best signal to noise ratio with minimum surface waves in a flat angle signal of the aforementioned type.

Other objects, uses and advantages will be obvious or become apparent from a consideration of the following detailed description and the application drawings.

However, it is to be distinctly understood that the specific drawing illustrations provided are supplied primarily to comply with the requirements of the Patent Laws, and that the invention is susceptible of embodiments that will be obvious to those skilled in the art, and which are intended to be covered by the appended claims.

GENERAL DESCRIPTION

Figure 1:
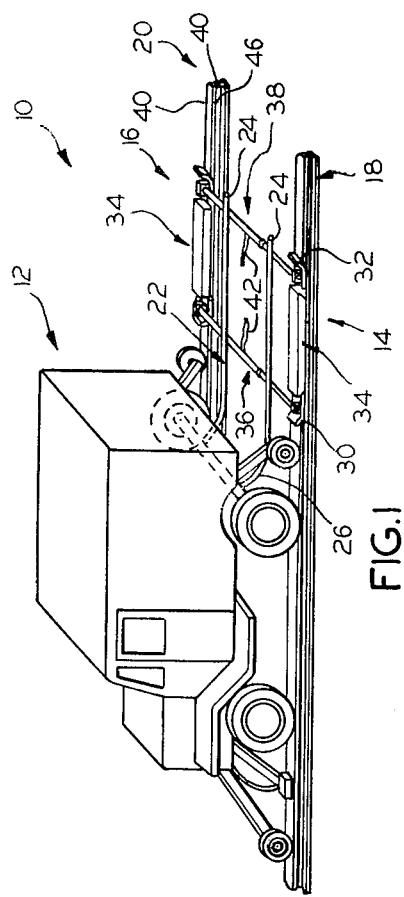
FIG. 1 is a diagrammatic perspective view illustrating an ultrasonic detector car and carriage assembly for use in practicing the present invention.

Reference numeral 10 of FIG. 1 generally indicates an ultrasonic progressive testing apparatus of the general type shown in my said U.S. Pat. No. 3,251,220, comprising a car 12 having operably connected thereto in trailing relation therewith carriages 14 and 16 for ultrasonically coupling to each track rail 18 and 20. The carriages 14 and 16 are are secured to the car 12 through a common suspension 22 that may be constructed in accordance with my U.S. Pat. No. 3,028,751, the disclosure of which is hereby incorporated herein by this reference. In general, the suspension 22 includes support arms 24 for connection to the rear axle of the car 12 through rubber joints 26 that accommodate both vertical and lateral swinging movement of the arms 24.

Each carriage comprises fore and aft spaced rail contacting guide shoes 30 and 32 interconnected by a trough frame or box 34.

Front and rear telescoping bar units 36 and 38 are suspended in crosswise relation from the support arms 24 and are connected to the fore and aft rail contacting shoes 30 and 32 of the respective carriages to establish a reference plane relative to the heads 40 of the respective track rails 18 and 20.

Each telescoping bar unit 36 and 38 is spring biased towards an elongated relation and is fitted with a motor driven cable 42 to cause each bar unit to contract progressively during elevation of the carriages by the cables 42 and to expand progressively during lowering of the carriages to their rail engaging positions.

With the exception of carriages 14 and 16, the structure shown in FIG. 1 is illustrative of the prior art and is thus shown only diagrammatically.

The carriages are of similar construction and a description of one of the carriage 14 and 16 is applicable to the second carriage, it being understood that the carriage 14 is adapted for cooperation with the track rail 18 with reference to the gauge edge 46 of its head 40, while the other carriage 16 is adapted for cooperation with the other track rail 20 with reference to the gauge edge 46 of the latter track rail.

Figure 3:
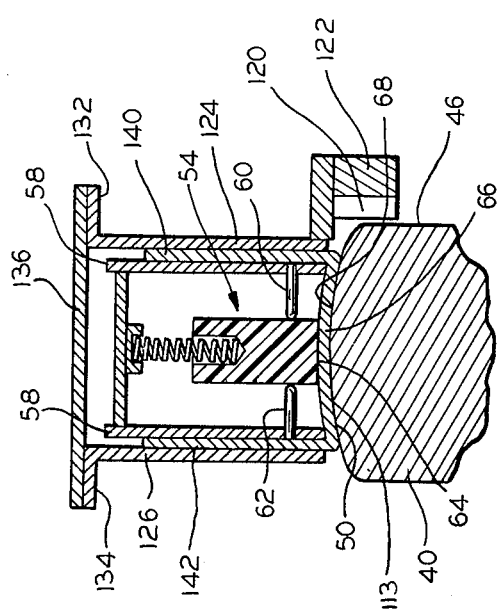
FIG. 3 is a diagrammatic transverse cross-sectional view of the carriage of FIG. 2 taken substantially along line 3—3 of FIG. 2.
Figure 2:
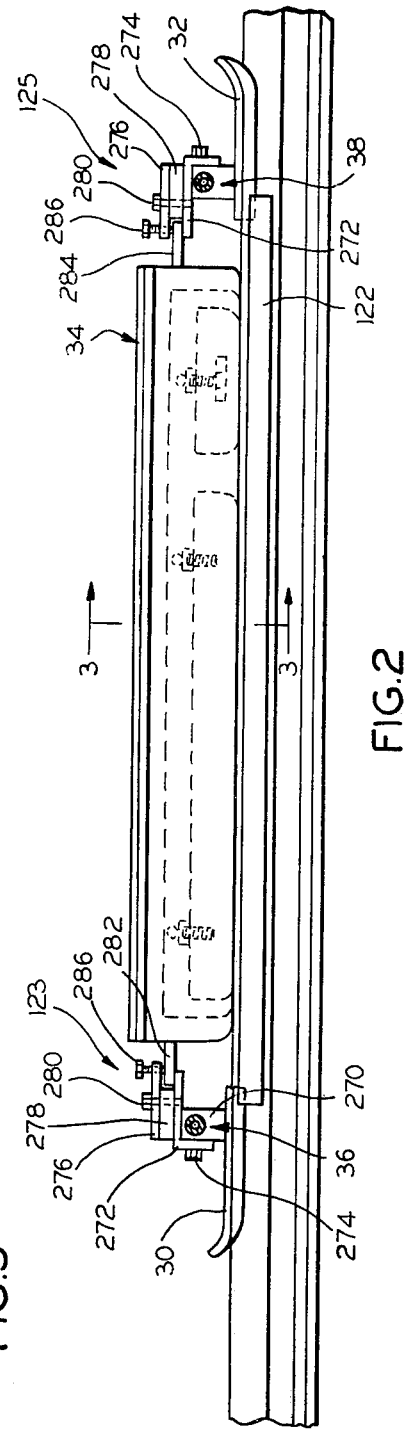
FIG. 2 is a side elevational view of one of the carriages, on an enlarged scale.

The showing of FIGS. 2 - 5 is concerned with the carriage 16 shown at the upper side of FIG. 1, and it will be seen that its box 34 mounts a diaphragm 50 (see FIGS. 3 and 5) on which is disposed the novel crystal array 52 comprising one embodiment of this invention shown incorporated in a fiberglass block 54 that extends lengthwise of the carriage and rests on the diaphragm 50 between a pair of runners 56 and 58 which maintain the diaphragm in conforming relation to the rail head for good ultrasonic contact, and which carry suitable guide posts 60 and 62 that operatively engage the sides of the block 54 to keep it located in a central position as the carriage slides along. As indicated in FIG. 3, the underside 64 of the block 54 is shaped to complement the shape that the underportion 66 of the diaphragm takes in conforming to top surface 68 of the rail head 40. Block 54 is biased against the diaphragm 50 and thus against the rail head by suitable means represented by compression springs 70 shown in the drawings.

In accordance with one embodiment of the present invention, the crystal array 52 generally comprises a first pair 79 of transducers in the form of crystals 80 and 82, that are respectively operatively associated with their respective wedges 84 and 86 which are located at the center of block 54 (which is intended to be approximately centered on the rail head 40) and are connected to act both as senders and receivers such that when the crystals are triggered the resulting signals are sent longitudinally of the rail in substantial parellelism with its longitudinal axis.

Array 52 also includes a second pair of transducers 87 in the form of the respective crystals 88 and 90 that are operably associated with the respective wedges 92 and 94, and are each connected both as senders and receivers and disposed to direct their signals in a canted direction relative to the longitudinal axis of the rail that is at an angle in the range of from 12° to 22°, and preferably about 19°, with respect to the longitudinal axis of the rail. The transducers 87 are thus oppositively canted, relative to the longitudinal axis of the rail, and preferably at angle of about 19 degrees, and in the direction of the rail head gauge edge 46 for this purpose. As indicated in FIG. 4, the signals of the respective transducers 87 act forwardly and rearwardly, but with the canted angulation indicated, in the direction of the rail gauge edge.

Further in accordance with this invention, the transducers 79 and 87 are located within the block 54 so that the respective crystals 80, 82, 88 and 90 will be at the center of the block 54 and thus are located at the center of the rail head 40.

Figure 4:
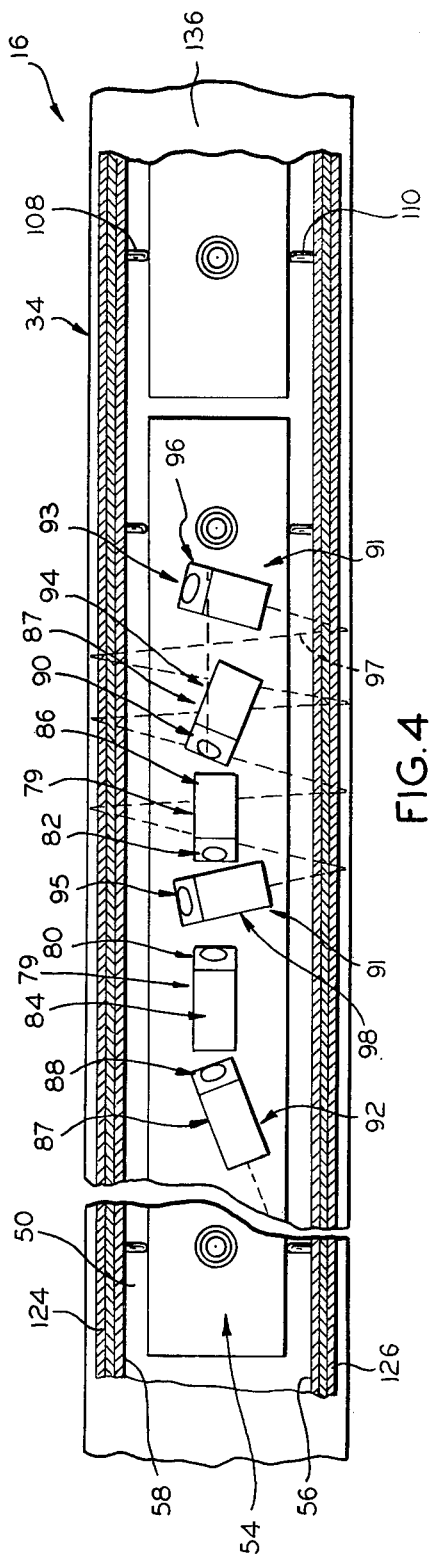
FIG. 4 is a diagrammatic horizontal cross-sectional view taken through the carriage of FIG. 2 in which the transducers and their associated parts are shown largely in block diagram form.

Array 52, further in accordance with the embodiment of FIG. 1 - 5 of this invention, includes a pair of transducers 91 comprising crystals 93 and 95 operably associated with the respective wedges 96 and 98, with the crystal 93 being connected to be a sender and the crystal 95 connected to be a receiver. The respective transducers 91 are oppositely angled, at 80° angles relative to the longitudinal axis of the rail, such that the signal emitted by the crystal 93 makes the zig-zag path indicated at 97, wherein the signal is initially directed to the gauge edge 46 of the rail head and bounces back and forth across the rail head for pick up by the crystal 95. Positioning the transducers 93 and 95 to provide for four bounces off rail gauge edge 40, as indicated in FIG. 4, is preferred for this embodiment for best results. Transducers 91 are positioned so that the sender crystal 93 applies its signal at the center of the block and said signal enters the center of the block for pick up by crystal 95. Thus transducers 91 act at the center of the rail head as well as transducers 79 and 87.

All the transducers 79, 87 and 91 are arranged for the flat angle ultrasonic signal generation that is disclosed in my said U.S. Pat. No. 3,251,220, and for this purpose, the respective crystals involved are oriented at an angle of incidence related to the material from which the wedges are formed so as to provide, at the best signal to noise ratio, shear waves acting at angles in the range of 80° to 85° relative to the level of the rail head surface 68 with minimum surface waves. The signal path involved is indicated at 99 in FIG. 5 for the right hand transducer 79. The sound energy on striking the rail fans into a beam 15° wide, thereby "lighting up" the rail in an efficient manner.

Operably associated with the carriage 16 is a second block 101 that is mounted within the runners 56 and 58 in the same manner as block 54 and carries vertical transducers 100 and 102, in the form of suitable crystals 104 and 106 that are both connected to be senders and receivers for directing their signals vertically of the track rail. The block 101 is centered within the runners 56 and 58 by suitable guides 108 and 110, and has its undersurface 112 contoured in the same manner as the undersurface 64 of block 54. Block 101 is biased against the rail head by suitable compression spring 70A.

The wedges of transducers 79, 87, 91, 100 and 102 preferably have their undersurfaces contoured in the same manner as the undersurface 112 of block 54 for improved efficiency.

The transducers 79, 87, 91, 100 and 102 are incorporated in a suitable ultrasonic circuiting arrangement of the general type disclosed in my U.S. Pat. No. 3,251,220 preferably utilizing the display techniques of my U.S. Pat. No. 3,156,111, whereby as the apparatus 10 moves along the track, the rails are progressively inspected for flaws that are detected by the ultrasonic system involved. The disclosure of said U.S. Pat. No. 3,156,111 is hereby incorporated herein by this reference.

As the apparatus 10 moves along the track, the signals provided by the transducers detect flaws within the rail. The beams provided by the transducers of crystal array 52 act as a flat angle of 80° – 85° relative to the level of the rail head surface 68, with the surface waves that would tend to be generated by such a flat angle being dampened by the diaphragm 50 and a film of water that is applied to the rail head surface 68 in advance of the respective carriages 14 and 16 by suitable equipment carried by the car 12, in accordance with said U.S. Pat. No. 3,251,220 (indicated at 113 in FIGS. 3 and 5).

It is to be noted that in the crystal array 52, all transducers are located to operate substantially at the center of the rail head, where best ultrasonic contact can be maintained. In this connection, when rail track is in regular use, the engagement that the car wheels make with the track has the result that, along the rail head top surface 68, there is a smoothly contoured wheel tread path that is generally centered along the rail head on straight track and provides the necessary smooth and clean rail surfacing that that is best adapted for ultrasonic contact with the rail. In accordance with this invention, all the transducers employed in array 52 are located and oriented so that the signals they generate operate through some or any point across the width of this path, which ordinarily has a width in the range of from approximately three quarter inch to approximately one and one half inches wide depending on the shape of the rail head and wheels riding on same, etc. In this disclosure and claims appended herein, when it is said that the transducers are located to operate at substantially at the center of the rail head, this means that the transducers are positioned and oriented so that their signals act on the rail along this rail head center path even though the signals involved may enter the rail head to one side of the other of the rail centerline. At curves this path may widen somewhat due to the binding action of the flange side of the wheel against the rail.

Further, in accordance with this invention, the wedges that the crystals of transducers 79, 87, and 91 act through are formed from a material which is relatively inefficient as a medium through which to send ultrasonic sound, whereby an improvement in the sound to noise ratio is obtained on the order of 15 percent, as compared with using a material which is an efficient medium through which to send ultrasonic sound. For this purpose, the wedges 84, 86, 92 and 94 and 96 and 98 are formed from a solid ultrasonic signal transmitting medium charged with a pulverant particulate material, such as powdered glass or powdered silicon carbide. Suitable materials for forming the wedges are urethane (which is preferred), epoxy, and plexiglas. The material selected should be charged with the particulate material in an amount in the range of from about one to about five percent by weight, with the particulate material being finely ground or powdered and uniformly disbursed throughout the wedge forming material. Other suitable particulate materials are finely ground sand, chalk, and pumice stone.

By charging the ultrasonic signal transmitting medium with a material such as powdered silicon carbide or powdered glass, the signal will be transmitted through the wedges in a variety of velocities, which breaks up the phase of the signal transmission, thus attenuating the transmission, and providing a desirable anrrow band width. While other powdered materials will also break noise sound velocities, the powdered materials specified are preferred as they seem to result in less noise and signal attenuation.

The resulting lossy nature of the wedges employed also helps eliminate the generation of surface waves at the respective transducers. The narrow band width from the electronic standpoint provided by utilizing the lossy wedges of this invention also contributes to the improvement in the signal to noise ratio.

As different materials used for the forming the wedges will pass the signals with different velocities, the wedges employed must be shaped to achieve the desired flat angle of signal transmission through the rail (80° – 85°) that is preferred. In accordance with this invention the angle of incidence selected for the individual wedges is with reference to the best signal to noise ratio at the angle of the signal in the rail, with reference to its head top surface 68, where compression waves are detected by the ultrasonic apparatus but do not predominate over shear waves.

Figure 7:
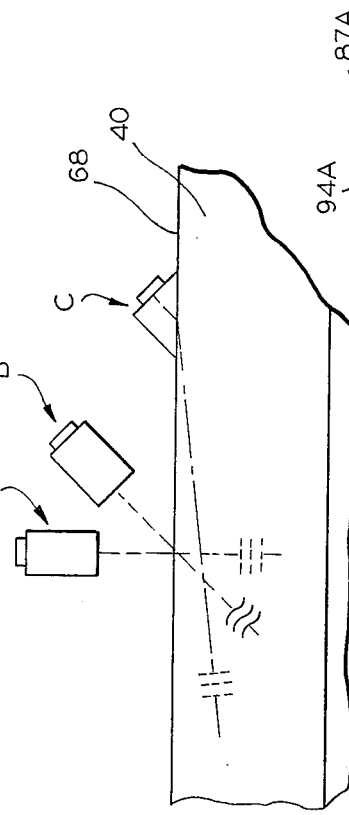
FIGS. 7 and 8 are diagrams employed to describe several basic aspects of the invention.

This is best explained by reference to FIG. 7 which diagrammatically illustrates transducers A, B, and C, at 90°, 45° and the desired flat angle signal producing positions relative to the rail head surface 68. The vertical transducer A (which is comparable to transducers 100 and 102) produces a compression wave oscillation in the rail without shear wave components; as transducer A is shifted to the position of transducer B, the first ten to fifteen degrees of shift produce little shear wave components in addition to compression waves. As the angle of transmission is shifted toward 25°, the compression wave is eliminated and only the slower shear wave is effective. However, as the angle of transmission is shifted beyond the 45° angle of transducer B to the angle of transducer C, the shear wave will attentuated somewhat and the compression wave will again be sensed. A signal sent longitudinally of the rail will again be sensed.

In accordance with the invention the angle of incidence selected for the wedges is that angle, with best signal to noise ratio, where the compression wave is just sensed by the ultrasonic apparatus involved, in terms of appearing on display apparatus of the type described in my said U.S. Pat. No. 3,156,111, without, however, the compression wave predominating, or the signal producing surface waves. In other words the shear waves should predominate, or preponderate, over the shear waves. Utilizing this critical angle, the ultrasonic signals provided avoid producing echoes from burns on the rail surface 68 or bolt holes in the web of the rail.

In this connection, the determination of this critical angle for any lossy material used to form the wedge is quite readily done as echoes for compression waves within the rail take 5 - 7 percent shorter time than shear waves, and thus the operator can readily determine when the angle is correct by watching for the compression wave to appear, in contrast to the predominant shear wave, when the correct angulation is being checked out.

Utilizing this principle, it has been found that when urethane is employed to form the wedges, the wedges should be shaped to provide an angle of incidence (of the signal through the wedges relative to the rail surface 68) in the range of from approximately 41° to approximately 59°. Where epoxy is employed the angle should be in the range of 25° – 20°, while where plexiglas is used, the angle should be in the range of 45° – 53°.

In this connection, a solid ultrasonic signal transmitting medium is preferred, as compared to liquid mediums, since it has been found that temperature variations vary the angle of incidence for liquid mediums (such as water).

In the embodiment of FIGS. 1 – 5, the wedges are formed from a suitable epoxy resin, such as the products sold under the trademark Epoxylite (Nos. 205 and 4102) by Epoxylite Corporation of El Monte, California.

Figure 5:
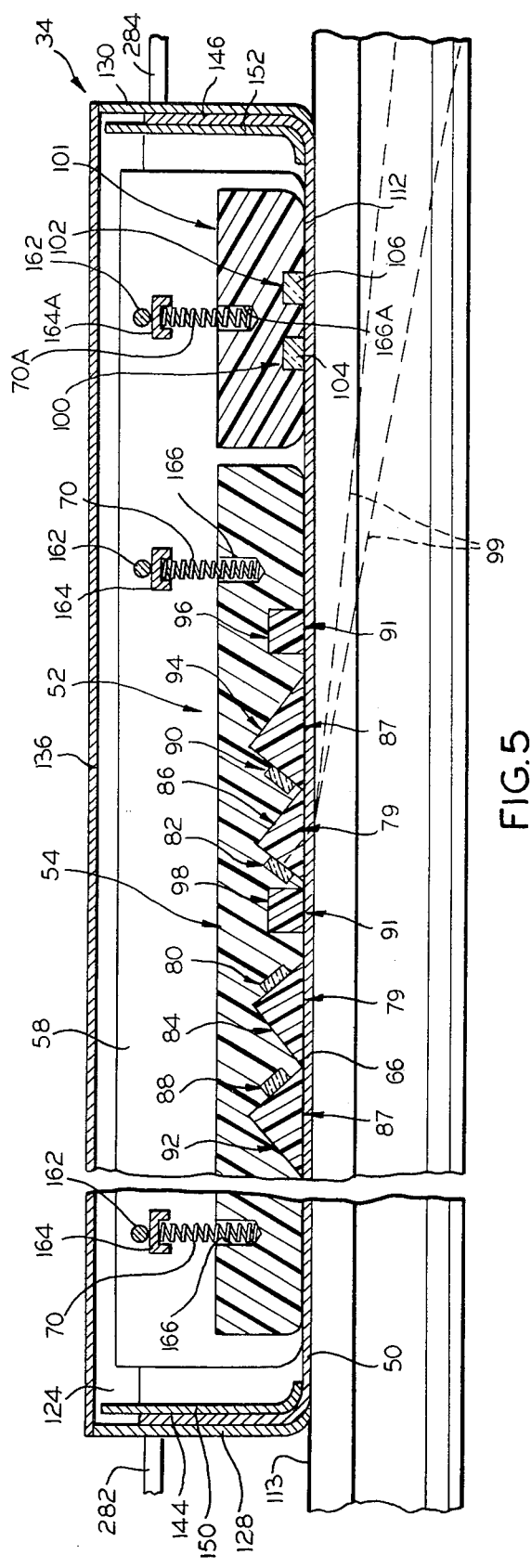
FIG. 5 is a vertical sectional view through the carriage and its crystal carrying blocks employed.

In operation, the transducers 79 effect transmission of their signals straight down the rail in the center of the rail head and down into the web as depicted by the signal path indicated for the right hand transducer 79 of FIG. 5. These two transducers are particularly efficient in locating small irregularities in the center of the rail head and more especially in all types of butt welded rail.

The transducers 87 locate all gauge edge defects, and are particularly useful in locating small defects lying in the lower corner of the rail head gauge edge, and those located in shelled and head checked territory and on worn curved rail. With the arrangement indicated for transducers 87 it is now possible to locate a gauge edge defect such as a hack saw mark 1/16th of an inch deep in the bottom corner of the rail head on the gauge side. Despite the sensitivity of operation provided by the transducers 87, these transducers do not provide objectionable pick up of the upset in all types of butt welds, as explained hereinafter.

The signal provided by the right hand transducer 91 of FIG. 4 follows the zig-zag path 99 that is indicated in FIG. 4 for pick up by the left hand transducer 91 provides contact with the rail that can be constantly monitored to show the relative efficiency of the ultrasonic contact that is being made by the carriage with the rail head. These transducers 91 provide a signal that is applied at the head of the rail, along the aforementioned center path of surface 68, and bounces back and forth between the edges of the rail head to the receiver transducer for reception and display purposes. The received result is a scatter propagation and not a direct interception of an ultrasonic transmission, with the received line on the B-scan tube being rough and jagged and not like a straight line like the base echo received from a vertical transducer (such as transducers 100 and 102) shooting straight into the rail head down to the rail base and back. However, the time of transmission of the signals of transducers 91 is uniform through a structural sound rail, and where, for instance, a vertical split is intercepted, even for a short distance, the display line undulates laterally, showing a change of time of ultrasonic transmission, which is the flaw detection basis on which transducers 91 operated (as distinguished from attenuation of an ultrasonic signal along a direct path.)

Transducers 91 are effective in locating vertical split heads and also horizontal split heads and large detail fractures.

While the vertical transducers 100 and 102 will find most split head defects which lie above the web of the rail, the transducers 91 are particularly useful in locating vertical split heads that appear on either side of the rail head which are relatively rare in occurance.

Figure 6:
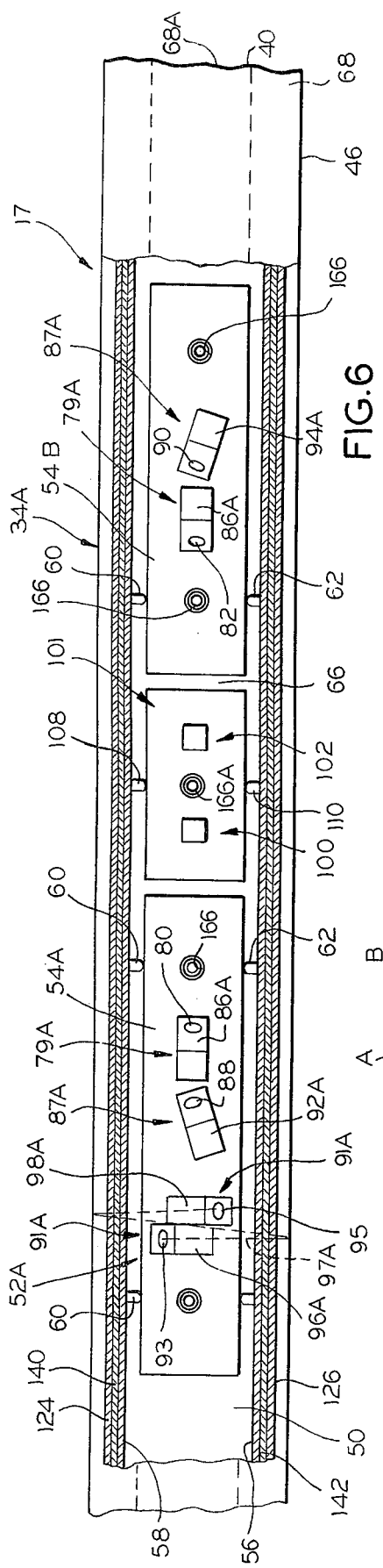
FIG. 6 is a view similar to that of FIG. 4 illustrating a modified form of the invention.

In the embodiment of FIG. 6, a modified and improved carriage 17 is provided that, except for the crystal array 52A and associated fiberglass blocks 54A and 54B mounting same, is essentially the same as carriages 14 and 16, as indicated by corresponding reference numerals where common parts are involved. Thus, the carriage 17 includes the box 34A that is the same as box 34 but is proportioned to accommodate the array 52A, and mounts diaphragm 50 on which is disposed the crystal array 52A, with the array resting on the diaphragm 50 between runners 56 and 58. Guide posts 60 and 62 are involved to keep the fiberglass blocks 54A and 54B centrally located as in the case of block 54.

The array 52A is incorporated in the respective discrete fiberglass blocks 54A and 54B, which are comparable to block 54, and block 101 which contains the vertical transducers 100 and 102 in the same manner as in the embodiment of FIGS. 1 – 5.

In the arrangement of FIG. 6, the block 101 is interposed between the blocks 54A and 54B. The array 52A comprises a first pair 79A of transducers in the form of crystals 80 and 82 that are respectively operably associated with their wedges 84A and 86A. Transducers 79A are comparable to transducers 79 except that wedges 84A, 86A are formed from urethane, and in accordance with the angle of incidence principle described hereinbefore, are shaped to provide an angle of incidence to the range of from 41 to 49 degrees. As indicated in FIG. 6, one of the transducers 79A is located in the block 54A while the other transducer 79A is located in the other block 54B.

Array 52A also comprises transducers 87A that are comparable to transducers 87 and thus comprise crystals 88 and 90 that are operably associated with the respective wedges 92A and 94A, though in this embodiment of the invention, the wedges 92A and 94A are formed from urethane and thus should be shaped to define an angle of incidence in the range of 41° to 40°. As indicated in FIG. 6, one of the transducers 87A is located in the block 54A while the other transducer 87A is located in the block 54B.

The transducers 79A and 87A aside from employing wedges made from urethane and having the indicated angle of incidence principle, operate in the same manner as transducers 79 and 87, respectively. It is preferred for this particular embodiment of the invention that the wedges for transducers 79A provide an angle of incidence of 49 degrees, while the wedges employed in transducers 87A is shaped to provide an angle of incidence of 41 degrees.

Array 52A further includes a pair of transducers 91A that are comparable to the transducers 91 but have the modified orientation diagrammatically indicated in FIG. 6 whereby the transducers 91A are disposed at an angle of 87 degrees with respect to the center line of rail and are in substantial parallelism as distinguished from being canted.

The transducers 91A comprise the respective crystals 93 and 95 operatively associated with the respective wedges 96A and 98A, with the wedges 96A and 98A being formed from urethane and thus being shaped to provide an angle of incidence in the range of 41° to 49°, with an angle of incidence of 43 degrees being employed in the illustrated embodiment.

The wedges 96A and 98A are mounted in the block 54A so as to be disposed in parallel vertical planes and are positioned in side by side relation such that their crystals are approximately ⅛ inch apart. In this connection, in the diagrammatic illustration of the drawings, the crystals are shown to be of smaller width than the wedges (for ease of illustration), but in practice, the width of the wedges exceeds the diameter of the crystals by about 1/16th of an inch.

Either transducer 91A may be the sender or receiver, and the three degree angulation of the transducers off right angle positioning with respect to the rail center line line results in the signal emitted by the sender crystal making the zig-zag path indicated at 97A wherein the signal is bounced off one edge of the rail head and across the rail against the other rail head edge and then to the receiver crystal involved.

The transducers 91A are particularly effective in locating vertical split heads as well as horizontal split heads and large detail fractures. The transducers 91A also effectively monitor the ultrasonic contact that the carriage 17 makes with the rail head.

The position of block 101 and its transducers in the form of FIG. 6 disposes the transducers 100 and 102 for convenience of the operator in reading the B scan display whereby hash marks resulting are more appropriately centered.

A suitable urethane material for making the wedges of the form of FIG. 6 is the liquid casting plastic product made and sold under the trademark clear cast by American Handicraft Company of Forth Worth, Texas, which product contains sytrene and carbamic esters.

The aforemention wheel tread path is shown diagrammatically in dashed lines in FIG. 6, at 68A. The width of the blocks 54, 54A, 54B and 101 is thus roughly the same as tread path 68A.

Figure 8:
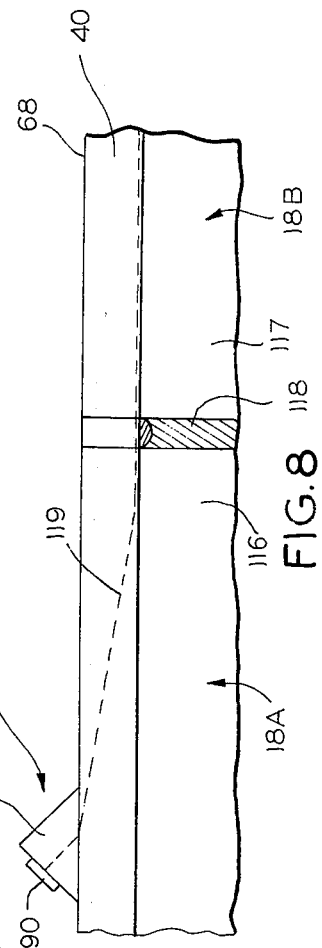

The optimum angle of operation contemplated by this invention insofar as the angle of incidence of the transducer wedges is concerned is of particular significance in connection with in-field welds which have a very heavy upset at the weld. FIG. 8 is a diagram illustrating what is involved wherein adjacent rails 18A and 18B have their ends 116 and 117 welded together which defines the upset or bulge indicated at 118, along the side of the joined rail web and under portion of the rail head. The weld joint across the sides and top of head 40 is smoothed off in practice, but not along the underportion of the head of the sides of the rail web, where the upset or protrusion involved has proved to be a problem in producing undersirable, misleading echoes.

It has been found that when the signal 119 of a transducer 87A is operating and is directed down the track in the manner previously described, the flat angle of the signal within the rail head in practice results in the bottom surfacing of the rail head along the garage edge of same keeping the signal within the rail heads. So that in effect the signal passes over the upset at the weld and thus no misleading echo is generated by the upset. Thus, the signal in question seems to be guided by the shape of the rail head down the rail and over the upset so that no echo results from the upset. This diagrammatically illustrated in FIG. 8.

SPECIFIC DESCRIPTION

The shoes 30 and 32 of the boxes 34 and 34A may be of a wear strip 120 suitably secured thereto which slides along the rail gauge edge 46 under the biasing action provided by the telescoping bar units 36 and 38, holding the respective carriages properly against the rail during movement of the same along the track. The respective wear strips 120 are connected together in tandem relation by bar 122.

The carriage boxes or troughs 34 and 34A are suitably connected to the respective shoes at either end of same, where indicated at 123 and 125, to support same and permit lateral adjustment of the box relative to the shoes, for adjusting the box 34 as desired laterally of the rail being tested. While the weight of boxes 34 34A is supported by the shoes of each box, the box is disposed as indicated in FIG. 3 so that the diaphragm 50 has firm engagement with the rail head. The connection of the box 34 to the shoes is diagrammatically illustrated in FIG. 3 wherein it will be seen that each shoe includes an upright member 270 (to which the respective telescoping bar units 36 and 38 are respectively connected) each having an angle member 272 adjustably secured thereto by suitable bolts 274. The respective angle members have secured thereto a top plate 276 resting against spacer 278, which are both secured in place on the respective members 272 by bolts 280. The respective flanges 282 and 284 of the boxes 34 and 34A rest on the respective angle members 272 and are clamped in place by set screws 286 applied to the respective top plates 276 at the desired positioning of the box 34 laterally of the rail.

The boxes 34 and 34A comprises side walls 124 and 126 (see FIG. 2) suitably joined to end walls 128 and 130, with the side walls 124 and 126 being suitably flanged as at 132 and 134, respectively for application thereto of a cover plate 136 that may be secured in place in any suitable manner as by employing bolts or the like.

The diaphragm 50 is formed from any suitable plastic rubber or the like flexible material and has a trough-like form defining side walls 140 and 142 and end walls 144 and 146, which are integral with the central portion 66 of the diaphragm on which the blocks 54 and (101 or 54A, 54B and 101) rest. The diaphragm side walls 140 and 142 are closely received between the respective runners 56 and 58 so that the central portion 66 is in overlying relation with the major portion of the transverse dimension of the rail head surface 68. At the forward end of the boxes 34 and 34A, the diaphragm wall 144 is held in place by a suitable clamp plate 150 while at the rear end of the box the diaphragm wall is held in place by suitable clamp plate 152, with the clamp plates 150 and 152 being suitably secured to the respective end walls 128 and 130 of the boxes or frames 34 and 34A.

The runners 56 and 58 are vertically disposed in the spaced apart relation indicated in FIGS. 3, 4, and 6 and are maintained in spaced apart relation by suitable cross rods 162 that interconnect the same as well as the action of the guide arms 60 and 62 and 108 and 110, which are carried by the respective runners 56 and 58, and engage the side walls of the respective blocks 54 and 101 (or 54A, 54B and 101). The runners 56 and 58 hold this central portion 166 of the diaphragm against the rail head surface 68 while permitting it to flex and distort as necessary to conform to changes in the rail surface contour. The guide posts or arms 60, 62, 108 and 110 maintain the position of the respective blocks 54, 101 54A and 54B against displacement laterally of the runners 56 and 58, but the fit is loose enough to permit these blocks to move vertically in following the contour of the rail head.

In the forms shown, the compression springs 70 act between suitable spring seats 164 suitably fixed to the respective cross rods 162, and recesses 166 formed in the blocks 54, 54A and 54C. Similarly, the compression spring 70A acts between suitable spring seat 164A and recess 166A formed in the block 101.

The crystals employed as part of the transducers described may be of the general type described in my said U.S. Pat. No. 3,251,220.

The crystals and wedges of the respective transducers are suitably embedded in the blocks 54, 54A and 54B to mount them in operating position in accordance with the principles herein stated. Similar remarks apply to the transducers of block 101, these being conventional vertical crystals.

Water is preferably applied to each rail adjacent the front of the vehicle 12 to allow sufficient time for the rail head to become wetted, and also just in advance of each box 34 and 34A, between the box and the forward shoe 30, for best results.

The foregoing description and the drawings are given merely to explain and illustrate the invention and the invention is not to be limited thereto, except insofar as the appended claims are so limited, since those skilled in the art who have the disclosure before them will be able to make modifications and variations therein without departing from the scope of the invention.

I claim:

1. In an ultrasonic apparatus for progressive railroad track rail flaw testing for detecting flaws in railroad track rails including a multi-element ultrasonic test signal pulse emitting and reverse path echo receiving assembly riding on the rail head in its operative position and comprising a plurality of separate ultrasonic transducer devices mounted in a carriage adapted to be coupled to the rail head in the assembly operative position by means of damping out surface waves on the rail head, through which means the ultrasonic signals are to act, the improvement wherein:

said transducer device comprise:
a first pair of transducer devices positioned for emitting ultrasonic test signal pulses forwardly and rearwardly of the rail along the center line of the rail head in the operative position of the assembly and for receiving reverse path echos of said pulses,
a second pair of transducer devices positioned for emitting ultrasonic test signal pulses forwardly and rearwardly of the rail in the operative position of the assembly and canted in opposite directions at an angle in the range of 12° to 22° with respect to the center line of the rail, and in the direction of the rail gauge edge and for receiving reverse path echoes of the pulses of the respective second pair of devices,
said transducer devices being located in the assembly to be disposed, in operative position of assembly, at the center of, and on top of, the top surface of the rail head and to act at an angle of incidence relative to the rail head top surface to produce in the rail as a result of their signal impulses ultrasonic waves travelling in the rail at flat angles on the order of 80° to 85° relative to the level of the rail head top surface. With the carriage being coupled to the rail top surface in the operative position of the assembly.

2. The improvement set forth in claim 1 wherein:
each transducer device of said transducer device pairs acts through its own wedge formed from a solid ultrasonic signal transmitting medium containing particulate material whereby velocities are imparted to the signal passing therethrough for minimizing noise levels.

3. The improvement set forth in claim 2 wherein:
said wedge each being formed to dispose the transducer which acts through same at the angle of incidence such that both shear and compression waves are produced in the rail acting at said flat angles with said shear waves preponderating.

4. The improvement set forth in claim 2 wherein:
said particulate material of each said wedge is pulverant and is widely disbursed throughout the respective wedges and comprises about 1 – 5 percent of same by weight.

5. The improvement as set forth in claim 3 wherein:
said wedges are formed from epoxy and the angle of incidence of said wedges is in the range of 25° – 30°.

6. The improvement set forth in claim 3 wherein:
said wedges are formed from urethane and the angle of incidence of said wedges is in the ranges of 41° – 49°.

7. The improvement set forth in claim 3 wherein:
said wedges are formed from plexiglass and the angle of incidence of said wedges is in the range of 45° – 53°.

8. The improvement set forth in claim 3 wherein:
said transducer devices of said pairs and their respective wedges are mounted in a fiberglass block carried by the carriage,
said block having its underside contoured to complement the contour of the rail head top surface,
and means for biasing said block against the rail head top surface when the assembly is in its operative position.

9. The improvement set forth in claim 3 wherein:
said carriage comprises a frame mounted on forward and rearward shoes riding on the rail head,
said frame mounting a diaphragm that is interposed between said block underside and the rail head top surface when the assembly is in its operative position,
and including means for forming a film of water on the rail head top surface in advance of said carriage when the assembly is in its operative position.

10. The improvement set forth in claim 1 wherein said transducer devices further comprise:
a third pair of transducer devices,
one of said third pair of transducer devices being positioned for emitting ultrasonic test signal pulses canted at an angle of approximately eighty degrees with respect to the centerline of the rail, and in the direction of the rail gauge edge, in the operative position of the assembly,
and the other of said third pair of transducer devices being canted in the opposite direction from said one device of said third pair of devices and being positioned at an angle of approximately eighty degrees with respect to the centerline of the rail, and in the direction of the rail gauge edge,
said devices of said third pair of devices being spaced longitudinally of the assembly for permitting the signal pulses of said one device of said third pair of devices to make a zigzag path across the rail head,
said devices of said third pair of devices being located in the assembly to be disposed, in the operative position of the assembly, at the center of, and on top of, the top surface of the rail head and to act at an angle of incidence relative to the rail head top surface to produce in the rail as a result of their signal impulses ultrasonic waves travelling at flat angles on the order of 80° to 85° relative to the level of the rail head top surface.

11. The improvements set forth in claim 10 wherein:
said spacing of said devices of said third pair of devices permits four bounces of the signal thereof on the rail gauge edge.

12. The improvement set forth in claim 1 wherein said transducer devices further comprise:
a third pair of transducer devices,
one of said third pair of transducer devices being positioned for emitting ultrasonic test signal pulses canted at an angle of approximately eighty seven degrees with respect to the centerline of the rail, and in the direction of the rail gauge edge, in the operative position of the assembly,
and the other of said third pair of transducer devices being disposed in substantial parallelism with said one device of said third pair of devices and comprising an echo receiver directed at the other rail edge,
said devices of said third pair of devices being in close adjacency longitudinally of the assembly with said canting thereof permitting the signal pulses of said one device of said third pair of devices to make a zigzag path across the rail head,
said devices of said third pair of devices being located in the assembly to be disposed, in the operative position of the assembly, at the center of, and on top of, the top surface of the rail head and to act at an angle of incidence relative to the rail head top surface to produce in the rail as a result of their signal impulses ultrasonic waves travelling at flat angles on the order of 80° to 85° relative to the level of the rail head top surface.

13. In an ultrasonic apparatus for progressive railroad track rail flaw testing for detecting flaws in railroad track rails including a multi-element ultrasonic signal pulse emitting and echo receiving assembly riding on the rail head in its operative position and comprising a plurality of separate ultrasonic transducer devices mounted in a carriage adapted to be coupled to the rail head in the operative position of the assembly by means for damping out surface waves on the rail head, through which means the ultrasonic signals are to act, the improvement wherein:
said transducer devices comprise:
a pair of transducer devices,
one of said pair of transducer devices being positioned to emit ultrasonic test signal pulses canted at an angle of approximately eighty seven degrees with respect to the centerline of the rail and in the direction of the rail gauge edge, in the operative position of the assembly,
and the other of said pair of transducer devices being disposed in substantial parallelism with said one device of said pair of devices and comprising an echo receiver illustrated at the other rail edge;
said devices of said pair of devices being in close adjacency longitudinally of the rail in the operative position of the assembly, with said canting thereof permitting the signal pulses of said one device of said pair of devices to make a zigzag path across the rail head,
said pair of transducer devices being located in the assembly to be disposed, in the operative position of the assembly, at the center of, and on top of, the top surface of the rail head and to act at an angle of incidence relative to the rail head top surface to produce in the rail as a result of their signal impulses ultrasonic waves travelling at flat angles on the order of 80° to 85° relative to the level of the rail head top surface,
whereby vertical split heads in the rail are identified by a change in time of the ultrasonic reception of the echo sensed by said receiver.

14. The improvement set forth in claim 13 wherein:
said spacing of said devices of said pair of devices permits one bounce of the signal thereof off the rail gauge edge in the operative position of the assembly.

15. The improvement set forth in claim 14 wherein:
each transducer device of said transducer device pair acts through its own wedge formed from a solid ultrasonic signal transmitting medium containing pulverant particulate material whereby velocities are imparted to the signal passing therethrough for minimizing noise levels, said wedges each being formed to dispose the transducer which acts through same at the angle of incidence such that both shear and compression waves are produced in the rail acting at said flat angles with said shear waves preponderating.

16. The improvement set forth in claim 15 wherein:
said particulate material of each said wedge is widely disbursed throughout the respective wedges and comprises about 1 – 5 percent of same by weight.

17. The improvement set forth in claim 10 wherein:
Each of said transducer devices of said pairs act through its own wedge formed from an ultrasonic transmitting medium comprising epoxy containing particulate material whereby velocities are imparted to the signal passing therethrough for minimimizing noise levels.

18. The improvement set forth in claim 17 wherein:
said transducer devices of said pairs and their respective wedges are mounted in a fiberglass block, said block having its underside contoured to complement the contour of the rail head top surface, and means for biasing said block against the rail head top surface when the assembly is in its operative position.

* * * * *

UNITED STATES PATENT OFFICE
CERTIFICATE OF CORRECTION

Patent No. 3,962,908          Dated June 15, 1976

Inventor(s)     IVAN L. JOY

It is certified that error appears in the above-identified patent and that said Letters Patent are hereby corrected as shown below:

Column 9, line 17, "$40°$" should read ---- $49°$ ----.

Signed and Sealed this

Second Day of November 1976

[SEAL]

Attest:

RUTH C. MASON
*Attesting Officer*

C. MARSHALL DANN
*Commissioner of Patents and Trademarks*